(12) United States Patent
 Choi et al.

(10) Patent No.: US 9,867,543 B2
(45) Date of Patent: Jan. 16, 2018

(54) ADJUSTABLE ANATOMY DISPLAY TABLE

(71) Applicant: Anatomage Inc., San Jose, CA (US)

(72) Inventors: Woncheol Choi, San Jose, CA (US);
Kristopher Thomson, Foster City, CA (US); Sean Pacheco, Fremont, CA (US)

(73) Assignee: Anatomage Inc., San Jose, CA (US)

( * ) Notice: Subject to any disclaimer, the term of this patent is extended or adjusted under 35 U.S.C. 154(b) by 432 days.

(21) Appl. No.: 14/260,769

(22) Filed: Apr. 24, 2014

(65) Prior Publication Data
US 2015/0309530 A1 Oct. 29, 2015

(51) Int. Cl.
*G06F 1/16* (2006.01)
*A61B 5/00* (2006.01)
*A61B 6/04* (2006.01)
*A61G 13/04* (2006.01)
*A61B 5/055* (2006.01)

(52) U.S. Cl.
CPC ............ *A61B 5/0073* (2013.01); *A61B 5/742* (2013.01); *A61B 6/04* (2013.01); *A61G 13/04* (2013.01); *A61B 5/055* (2013.01)

(58) Field of Classification Search
CPC ....... A61B 5/0073; A61B 5/742; A61B 5/055; A61B 8/08; A61B 19/5244; A61B 6/04; G06F 1/16; G06F 1/1601; G01S 15/8993; A61G 13/04
See application file for complete search history.

(56) References Cited

U.S. PATENT DOCUMENTS

| | | | | |
|---|---|---|---|---|
| 2,049,271 A | * | 7/1936 | Nelson | A61B 6/04 378/179 |
| 3,868,103 A | * | 2/1975 | Pageot | A61G 13/02 137/596 |
| 5,023,899 A | * | 6/1991 | Ohlson | A61B 6/022 378/177 |
| 6,027,247 A | * | 2/2000 | Tachi | A61B 6/0457 378/177 |
| 6,031,888 A | * | 2/2000 | Ivan | A61B 6/4464 378/196 |
| 6,450,684 B2 | * | 9/2002 | Kobayashi | G03B 42/02 378/177 |
| 6,851,851 B2 | * | 2/2005 | Smith | A61B 6/0457 378/167 |
| 6,934,361 B2 | * | 8/2005 | Ohkoda | G03B 42/02 378/177 |
| 7,331,712 B2 | * | 2/2008 | Fischer | A61B 6/04 250/519.1 |
| 2011/0046935 A1 | * | 2/2011 | Sugaya | G06F 19/3437 703/11 |
| 2014/0357984 A1 | * | 12/2014 | Wallace | A61B 5/062 600/424 |

* cited by examiner

Primary Examiner — Michael Zarroli

(57) ABSTRACT

An adjustable anatomy display table is disclosed. According to one embodiment, the adjustable anatomy table includes a display configured to visualize the anatomy in a real size, a base configured to support the display, and an adjustable mechanism that mechanically couples the display to the base. The adjustable mechanism is configured to adjust a position of the display relative to the base.

19 Claims, 6 Drawing Sheets

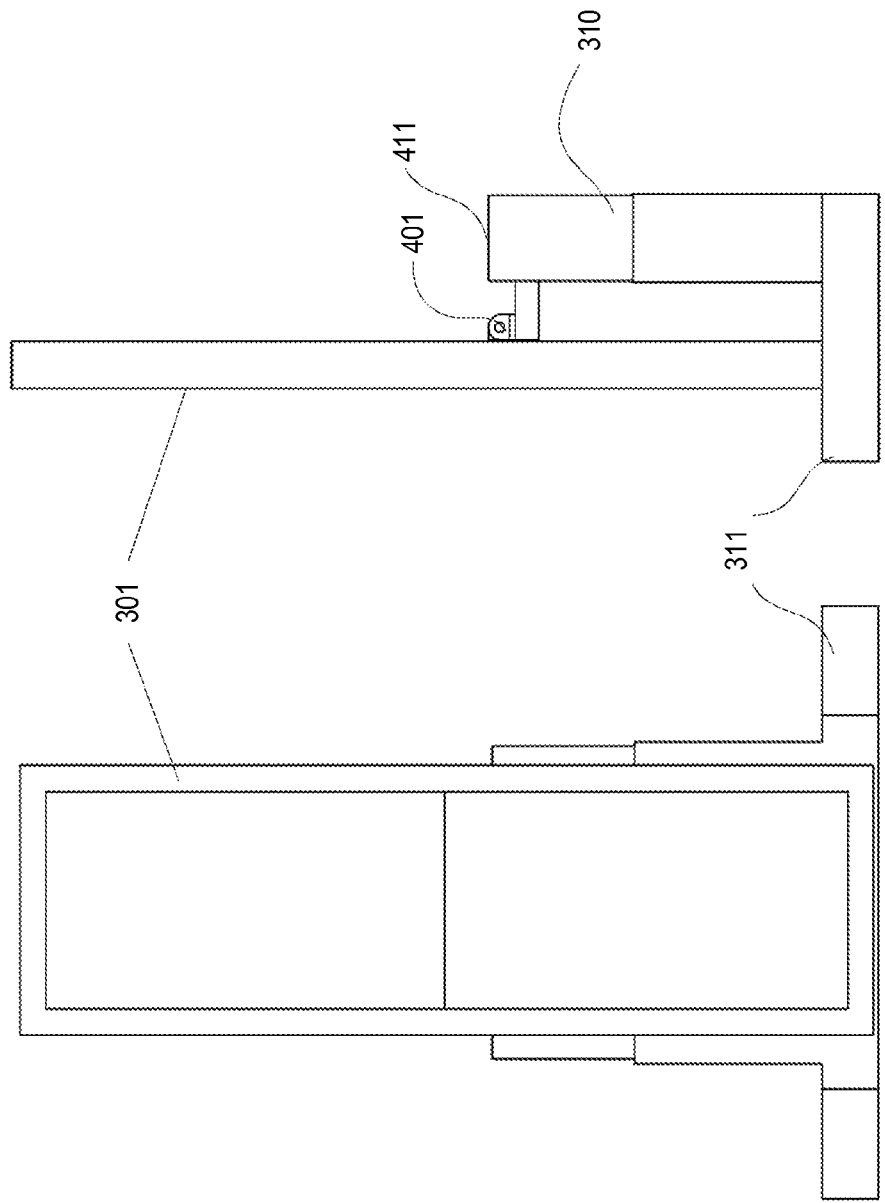

ADJUSTABLE ANATOMY DISPLAY TABLE

FIELD

The field of the present disclosure relates generally to a medical imaging device, and more particularly, to an adjustable anatomy display table.

BACKGROUND

A variety of medical scanners is used to generate clinical images. The scanned images include anatomical features such as organs, tissues, blood vessels, and other components of human anatomy. Such medical scanners include, x-ray, computed tomography (CT), magnetic resonance imaging (MRI), ultrasound, positron emission tomography (PET) and single photon emission computed tomography (SPECT). Radiologists and physicians analyze scanned images for diagnosis and treatment.

Scanned images using a medical scanner consist of two-dimensional (2D) slices. A medical imaging device is used to generate three-dimensional (3D) volume data of human anatomy from a series of 2D slices obtained from a medical scanner. The 3D volume data provides more intuitive and useful information of a patient's anatomy. An imaging tool or imaging software provides intuitive means to navigate through the tortuous and complex human anatomy. The imaging tool can show cross-sectional views of the 3D volume data from various angles and positions and virtually dissect or selectively view an area of interest via image processing on the 3D volume data.

Medical knowledge is very complex and scattered in various subjects in textbooks. Medical students (e.g., medical, dental, nursing, physiotherapy) require years of practice and experience to apply their knowledge on clinical cases. One of the main challenges for medical students is the process of linking all the knowledge that they have gained from their studies and applying it to specific cases. Typically, learning in a medical college is done in several subjects such as anatomy, pathology, microbiology and pharmacology. Each student has to mentally put the learned information together to get from diagnosis of a problem to the treatment and case management.

Knowledge of the human anatomy is very important to clinicians and medical students. Learn human anatomy from a life-sized model or a cadaver is expensive, and is not a viable option in some countries due to religious reasons.

SUMMARY

An adjustable anatomy display table is disclosed. According to one embodiment, the adjustable anatomy table includes a display configured to visualize the anatomy in a real size, a base configured to support the display, and an adjustable mechanism that mechanically couples the display to the base. The adjustable mechanism is configured to adjust a position of the display relative to the base.

The above and other features, including various novel details of implementation and combination of elements, will now be more particularly described with reference to the accompanying drawings and pointed out in the claims. It will be understood that the particular methods and apparatuses are shown by way of illustration only and not as limitations. As will be understood by those skilled in the art, the principles and features explained herein may be employed in various and numerous embodiments.

BRIEF DESCRIPTION OF THE DRAWINGS

The accompanying drawings, which are included as part of the present specification, illustrate various embodiment of the present disclosure and together with the general description given above and the detailed description of the embodiment given below serve to explain and teach the principles of the present disclosure.

FIG. 4A illustrates a front view of an exemplary adjustable anatomy table in a vertical configuration, according to one embodiment;

FIG. 4B illustrates a side view of an exemplary adjustable anatomy table in a vertical configuration, according to one embodiment;

Figure 1A:
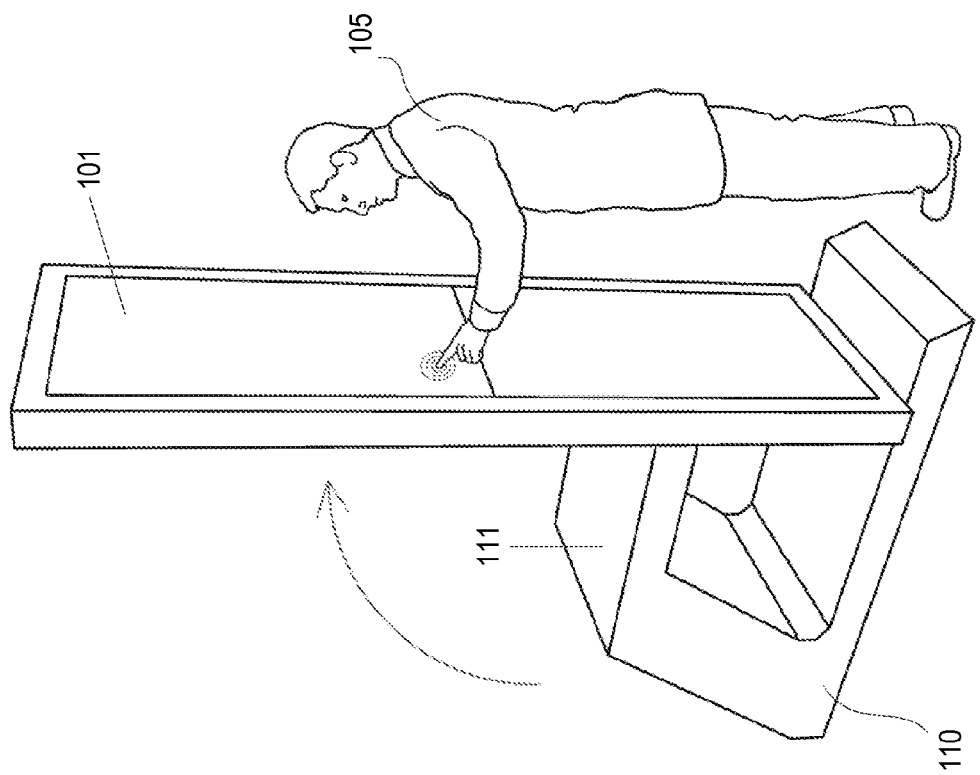
FIG. 1A illustrates an exemplary adjustable anatomy table, according to one embodiment.

It should be noted that the figures are not necessarily drawn to scale and that elements of structures or functions are generally represented by reference numerals for illustrative purposes throughout the figures. It also should be noted that the figures are only intended to facilitate the description of the various embodiments described herein. The figures do not describe every aspect of the teachings described herein and do not limit the scope of the claims.

DETAILED DESCRIPTION

An adjustable anatomy display table is disclosed. According to one embodiment, the adjustable anatomy table includes a display configured to visualize the anatomy in a real size, a base configured to support the display, and an adjustable mechanism that mechanically couples the display to the base. The adjustable mechanism is configured to adjust a position of the display relative to the base.

In the following description, for purposes of clarity and conciseness of the description, not all of the numerous components shown in the schematic are described. The numerous components are shown in the drawings to provide a person of ordinary skill in the art a thorough enabling disclosure of the present disclosure. The operation of many of the components would be understood to one skilled in the art.

Each of the additional features and teachings disclosed herein can be utilized separately or in conjunction with other features and teachings to provide the present table game. Representative examples utilizing many of these additional features and teachings, both separately and in combination, are described in further detail with reference to the attached drawings. This detailed description is merely intended to teach a person of skill in the art further details for practicing various aspects of the present teachings and is not intended to limit the scope of the claims. Therefore, combinations of features disclosed in the following detailed description may not be necessary to practice the teachings in the broadest sense and are instead taught merely to describe particularly representative examples of the present teachings.

The methods presented herein are not inherently related to any particular computer or other apparatus. Various general-purpose systems may be used with programs in accordance with the teachings herein, or it may prove convenient to construct more specialized apparatus to perform the required method steps. The required structure for a variety of these systems will appear from the description below. In addition, the present disclosure is not described with reference to any particular programming language. It will be appreciated that a variety of programming languages may be used to implement the teachings of the present disclosure as described herein.

Moreover, the various features of the representative examples and the dependent claims may be combined in ways that are not specifically and explicitly enumerated in order to provide additional useful embodiments of the present teachings. In addition, it is expressly noted that all features disclosed in the description and/or the claims are intended to be disclosed separately and independently from each other for the purpose of original disclosure, as well as for the purpose of restricting the claimed subject matter independent of the compositions of the features in the embodiments and/or the claims. It is also expressly noted that all value ranges or indications of groups of entities disclose every possible intermediate value or intermediate entity for the purpose of original disclosure, as well as for the purpose of restricting the claimed subject matter. It is also expressly noted that the dimensions and the shapes of the components shown in the figures are designed to help understand how the present teachings are practiced but are not intended to limit the dimensions and the shapes shown in the examples.

A series of scanned images of a human body by a medical scanner such as a computed tomography (CT) scanner and a magnetic resonance imaging (MRI) scanner is of a two-dimensional (2D) nature. The scanned images need to be extrapolated and reconstructed to create volume data for three-dimensional (3D) anatomical structures. Using the 2D slices of scanned images or even 3D reconstructed anatomical structures are difficult to provide a conceptual and intuitive understanding of 3D anatomy. A medical imaging system with advanced browsing capabilities plays an increasingly important role in medical training, research and diagnostics. In particular, a 3D imaging system facilitates a better understanding of complex phenomena of the anatomy knowledge.

According to one embodiment, the present adjustable anatomy table is a human anatomy display device. The present adjustable anatomy table has a display that is properly sized to visualize a full size human anatomy in a 1:1 life size. However, it is apparent that the present adjustable anatomy table can be used to visualize other sizes, scales, and forms of images of different kinds without deviating from the scope of the present disclosure.

According to one embodiment, a digital human anatomy is constructed using volumetric visualization from slices of 2D images that are obtained from a medical scanner. The present adjustable anatomy table is capable of visualizing a realistic, accurate, and patient-specific human anatomy on the display. In one embodiment, the present adjustable anatomy table has dual displays arranged next to each other. The size and aspect ratio of the displays are determined to fit to a human size. Hence, the present adjustable anatomy table is capable of visualizing the human anatomy from a head to a toe in a 1:1 life size. According to one embodiment, the present adjustable anatomy table has a display that provides touch interactivity with a user. Based on a user's touch input on the display, the user can rotate, slice, zoom-in or zoom-out, the displayed images to reveal anatomical features including tissues, vessels, air ways, an internal organ, structure, etc. It is apparent that other types of input methods and devices may be used without deviating from the scope of the present disclosure, for example but are not limited to, a keyboard, a mouse, a voice input, a gesture input, an input using a wearable computer.

According to one embodiment, images displayed on the present adjustable anatomy table are acquired from medical images such as CT, MRI, PET, ultrasound, SPECT, etc. In another embodiment, images are obtained from real slices of a real human body by slicing a cadaver body with a tissue slicing machine, or photographs of cross sections of a human body. For example, images are obtained from a data set of cross-sectional photographs of a human body provided by the Visible Human Project of U.S. National Library of Medicine.

According to one embodiment, the present adjustable anatomy table is used for medical education by illustrating anatomy, pathology. Students can examine and explore the displayed 3D human anatomy on the present adjustable anatomy table, and visually examine human organs, tissues, blood vessels, and other components and their functional relationships. The touch interface allows the students to make an incision on the human anatomical structures and examine the internal structure of the human anatomy.

According to one embodiment, the present adjustable anatomy table is used for patient diagnosis. Since the present adjustable anatomy table runs an application that can open scanned 2D medical images and reconstruct them into 3D volume data. Radiologist and physicians review the reconstructed 3D volume data and images for diagnosis or treatment planning In addition, surgeon can review the image for diagnosis and treatment planning According to one embodiment, the present adjustable anatomy table is used for patient consultation. Patient-specific scanned medical images are loaded during patient consultation. Since the patient-specific images are shown in a realistic manner, present adjustable anatomy table provides an effective tool for patient consultation and communication.

According to one embodiment, the display of the present adjustable anatomy table is laid on flat table. The images shown on the display is consistent with a real patient lying on a bed. Thus, when a displayed image on the display is used for diagnostic and/or treatment planning purposes, the surgeon sees the patient's image in the same angle and size of the real patient in a surgical operatory. Therefore, the present adjustable anatomy table provides improved diagnostic and surgical procedures and reduces the possibility of making mistakes.

For an education use, the present adjustable anatomy table is also helpful. The displayed images on the display are consistent with the ways students experience during cadaver dissection. Students can stand around the present adjustable anatomy table for group education.

According to one embodiment, the present adjustable anatomy table is adjustable in various angles and positions. For example, the present adjustable anatomy table is positioned in a vertical configuration mimicking a human body in a standing up position. The adjustability of the present anatomy table is useful for applications such as an orthopedic application, in which case the display of a human body in a vertical position is more intuitive and beneficial in presenting a patient-specific case on the present adjustable anatomy table.

FIG. 1A illustrates an exemplary adjustable anatomy table, according to one embodiment. The adjustable anatomy table 100 has a display 101 placed over a base 110. A user 105 interacts with images shown on the display 101 via a touch-sensitive interface of the adjustable anatomy table 100. In one embodiment, the display 101 can include, but are not limited to, a cathode ray tube (CRT) display, a light emitting diode (LED) display, an organic LED (OLED) display, a gas plasma display, and a liquid crystal display (LCD). In one embodiment, the display 101 is a touch-sensitive display with capacitive or resistive touch sensors. In another embodiment, the display 101 is a non-touch-sensitive screen with one or more optical sensors to detecting a point of contact on the display 101.

Figure 1B:
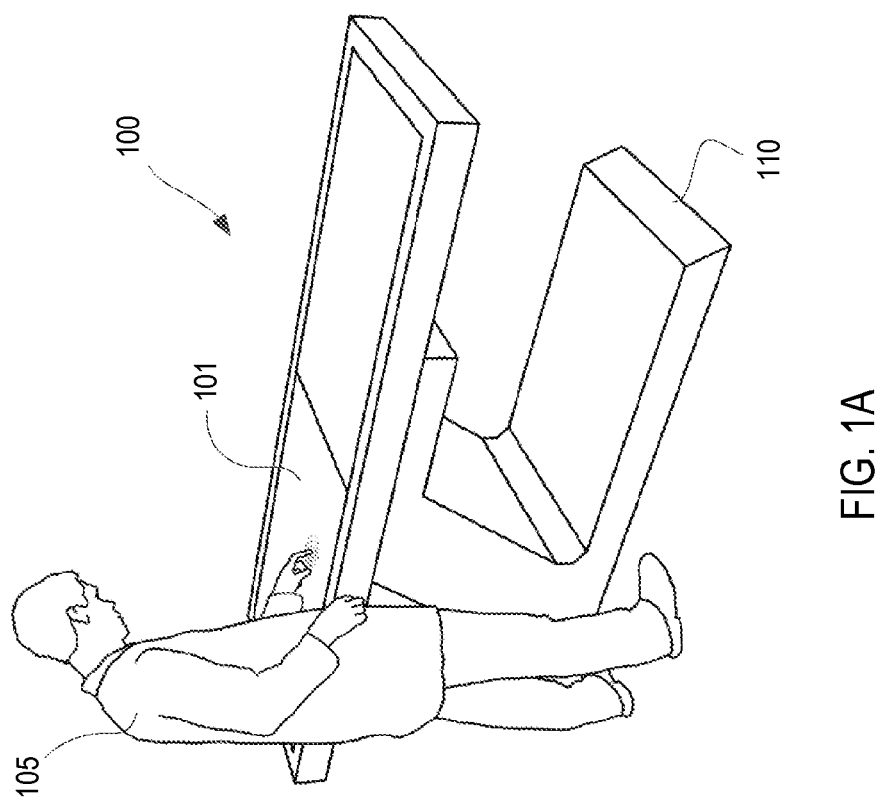
FIG. 1B illustrates an exemplary adjustable anatomy table in a vertical configuration, according to one embodiment.

FIG. 1B illustrates an exemplary adjustable anatomy table in a vertical configuration, according to one embodiment. The adjustable anatomy table 100 has a vertical tilting mechanism to tilt the display 101 in an upright position. In a default position, the display 101 lies flat on the surface 111 of the base 110. After adjustable anatomy table 100 is tilted in the vertical position by tilting the display 101 in the upright position until the display 101 is locked in place. The user 105 interacts with the adjustable anatomy table 100 in the upright position. In one embodiment, the adjustable anatomy table 100 has an adjustable locking mechanism such that the user tilts the display 101 at a desired angle between 0 and 90 degrees. In another embodiment, the adjustable anatomy table 100 has one or more locking mechanisms to lock the display 101 at predefined angles.

In one embodiment, the display 101 of the adjustable anatomy table 100 is sized to visualize a specific anatomy of a human or an animal. The size of the display and/or the base 110 may be appropriately sized depending on an intended application.

Figure 2A:
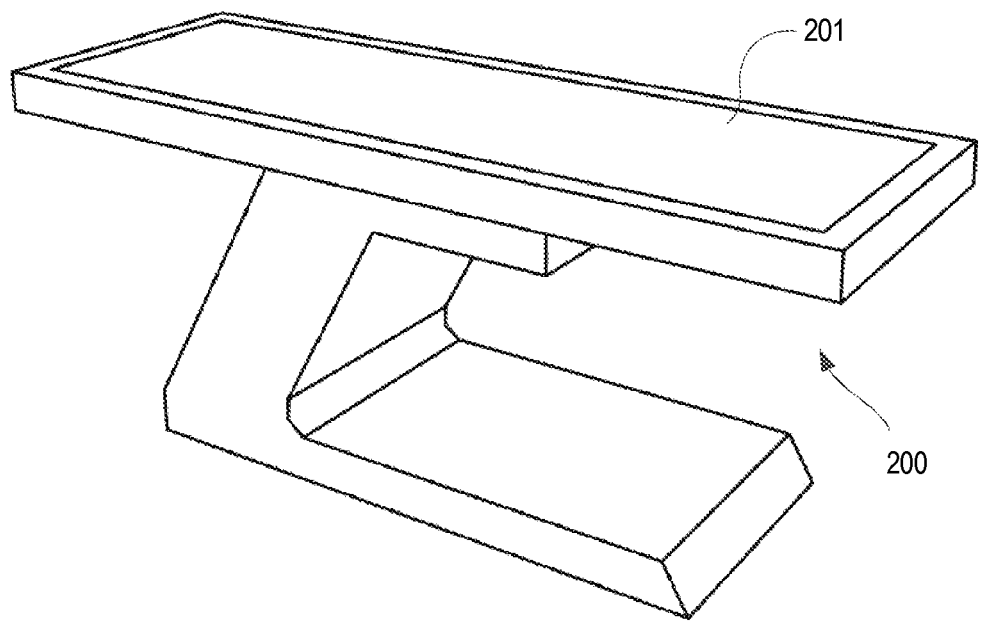
FIG. 2A illustrates an exemplary adjustable anatomy table with a single display, according to one embodiment.

FIG. 2A illustrates an exemplary adjustable anatomy table with a single display, according to one embodiment. The display 201 has a profile and an aspect ratio that are adequate for visualizing an entire life-sized human anatomy.

Figure 2B:
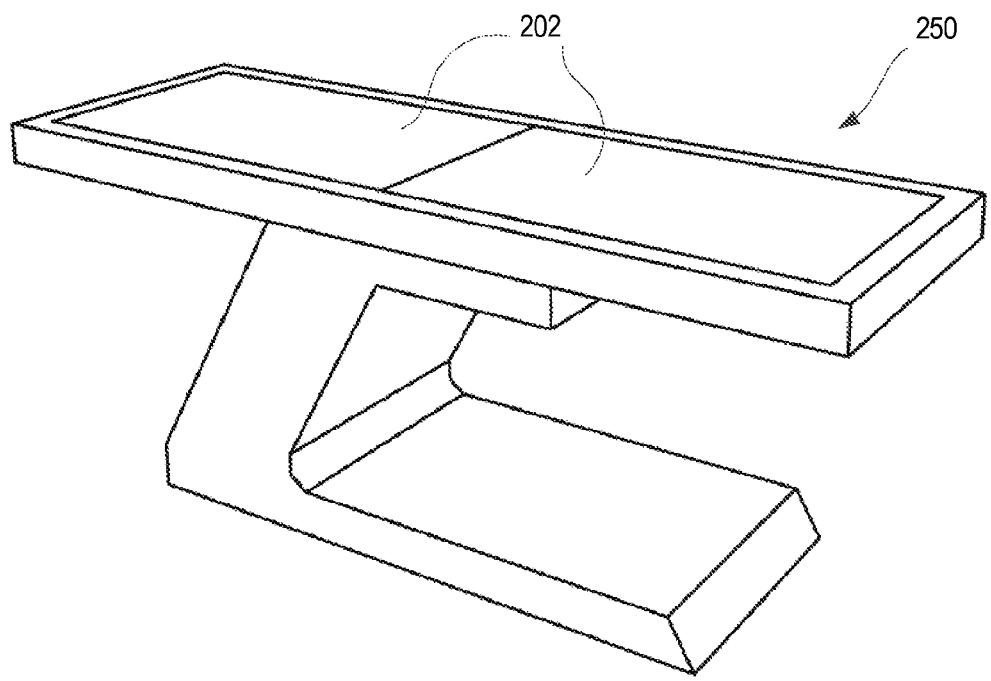
FIG. 2B illustrates an exemplary adjustable anatomy table with dual displays, according to one embodiment.

FIG. 2B illustrates an exemplary adjustable anatomy table with dual displays, according to one embodiment. The dual display adjustable anatomy table 250 includes dual displays 202 that are coupled together to form an aspect ratio that is adequate for visualizing an entire life-sized human anatomy. The dual displays 202 have a thin bezel to provide visual continuity between the displays. Smaller displays are typically cheaper than a single display that provides the same screen size. The dual screen example of FIG. 2B is shown for the illustration purpose only, and it should be understood that any size and number of displays may be combined to provide a surface size that is adequate for visualizing an entire life-sized human anatomy.

Figure 3:
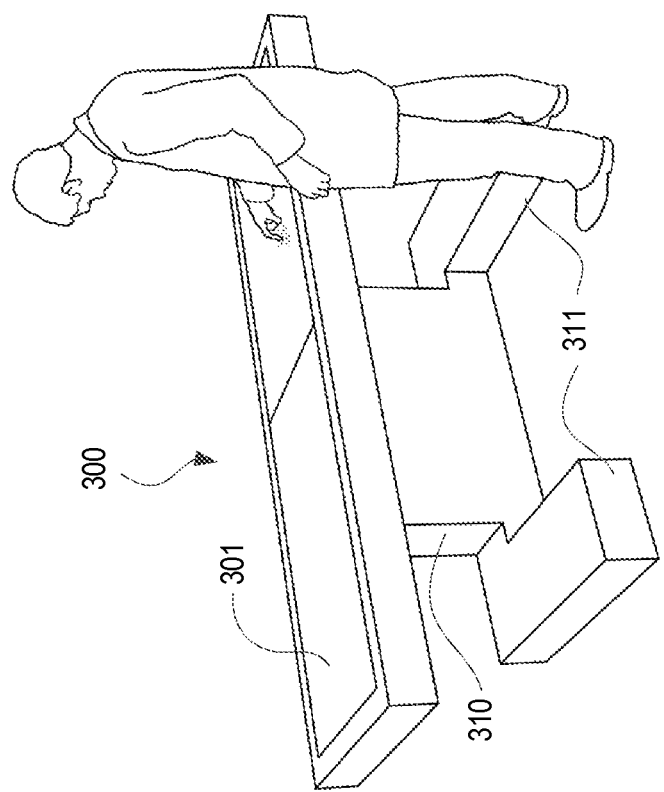
FIG. 3 illustrates an exemplary adjustable anatomy table with one or more adjustable features, according to one embodiment.

FIG. 3 illustrates an exemplary adjustable anatomy table with one or more adjustable features, according to one embodiment. The adjustable anatomy table 300 has a base 310 and one or more legs 311 that extend out from the base 310 to provide a firm stability to the adjustable anatomy table 300 in various configurations and positions. The adjustable anatomy table 300 may have one or more adjustable mechanisms (e.g., tilt, vertical up/down, rotation). Based on a configuration, the adjustable anatomy table 300 may include a mix and match of the adjustable mechanisms to provide a custom solution for an intended application. It is apparent that one of ordinary skilled person in the art would recognize that various sizes, shapes, and adjustable mechanisms may be implemented in an adjustable anatomy table without deviating from the scope of the present disclosure.

FIG. 4A illustrates a front view of an exemplary adjustable anatomy table in a vertical configuration, according to one embodiment. FIG. 4B illustrates a side view of an exemplary adjustable anatomy table in a vertical configuration, according to one embodiment. In one embodiment, the tilting mechanism 401 has a hinge member for pivotally coupling the display 301 to the frame of the base 310. The tilting mechanism 401 may include more than on hinge members and/or a shock absorber (e.g., a gas or liquid filled strut). In one embodiment, the tilting mechanism 401 has a gear mechanism (not shown) that can manually or automatically tilt the display 301. It is noted that a different type of tilting mechanism may be used without deviating from the scope of the present disclosure.

The tilting mechanism 401 provides a tilting adjustability of the display 301. In a horizontal position, the bottom surface of the display 301 touches with and sits on a flat surface 411 of the base 310. The locking mechanism (not shown) places the screen 310 in a locking position. The vertical tilting mechanism 401 may be made to operate manually or automatically by a servo motor.

Figure 5B:
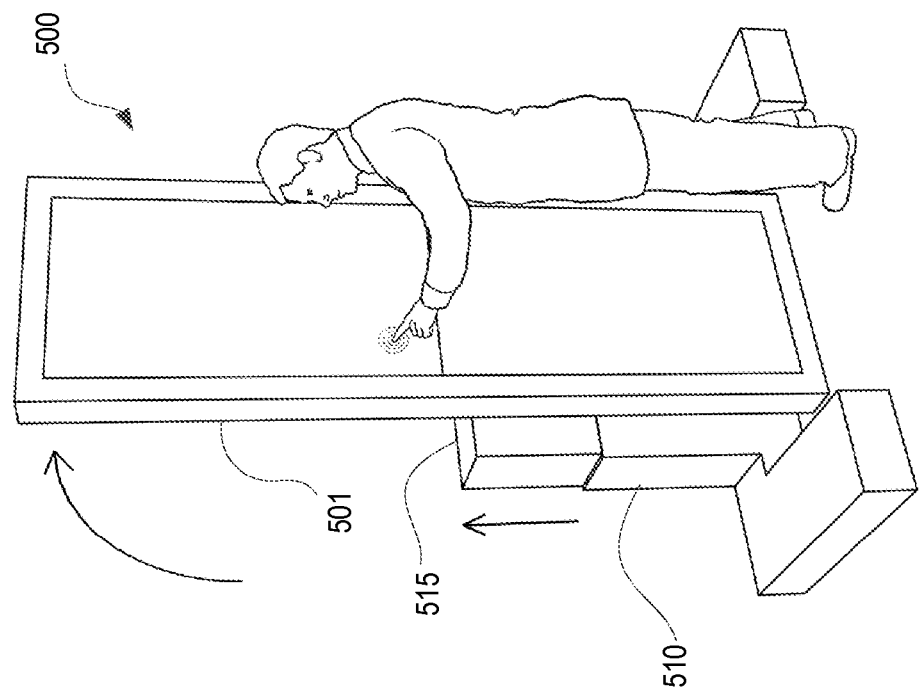
FIG. 5B illustrates a height adjustability of an exemplary adjustable anatomy table, according to one embodiment.
Figure 5A:
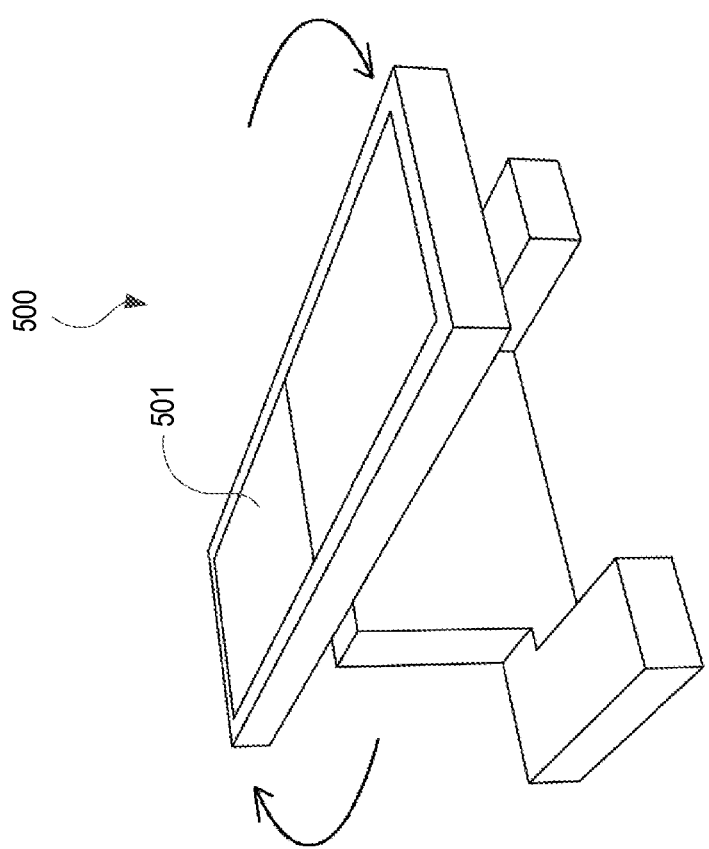
FIG. 5A illustrates a rotational adjustability of an exemplary adjustable anatomy table, according to one embodiment.

FIG. 5A illustrates a rotational adjustability of an exemplary adjustable anatomy table, according to one embodiment. In one embodiment, the adjustable anatomy table 500 includes a rotationally adjustable mechanism (not shown) to allow a user to rotate the display 501 in a horizontal position. The rotational adjustability of the adjustable anatomy table 500 is particularly useful for a group education session in an anatomy classroom. In one embodiment, the rotational adjustable mechanism is combined with a tilting adjustability that as shown in FIGS. 4A and 4B. In this case, the rotational and tilting adjustable mechanisms may independently operate, however the display 501 may be tilted only in a specific rotational position, for example, at a rotational angle of 0 or 180 degrees. The tilting mechanism may be locked until the display 501 is positioned at a designated rotational angle to provide safety. In one embodiment, the tilting mechanism is implemented on a rotating platform that provides the rotational adjustability. In another embodiment, adjustable anatomy table 500 has the rotational adjustable mechanism without a tilting mechanism.

FIG. 5B illustrates a height adjustability of an exemplary adjustable anatomy table, according to one embodiment. The adjustable anatomy table 500 can move vertically up and down and be locked at a desired height. In one embodiment, the height and rotational mechanisms as well as the tilting mechanism are combined together to provide a multi-dimensional adjustability to the anatomy table 500. The base 510 of the adjustable anatomy table 500 includes the height adjustable mechanism 515 that can slide in and out of the base 510 providing a user with a height adjustability of the display 510. For example, the adjustable anatomy table 500 can rotate with a rotating mechanism and move up and down using the height adjustable mechanism 515 while in an upright vertical position with a tilting mechanism.

Figure 5C:
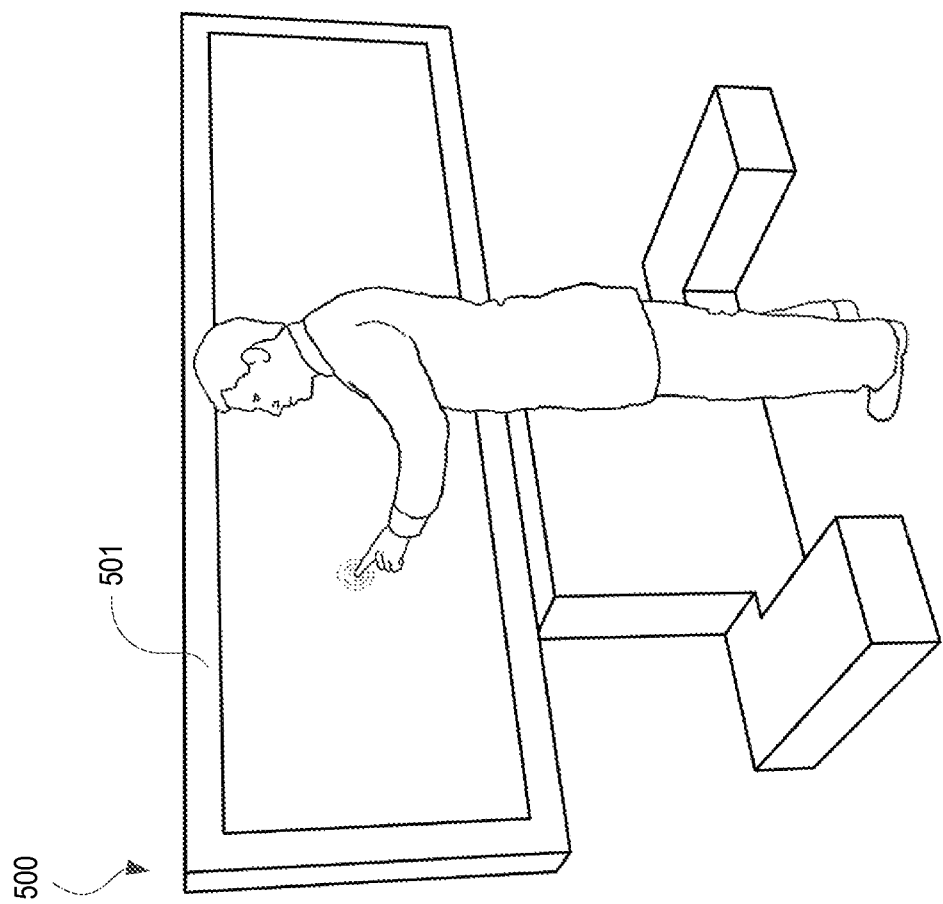
FIG. 5C illustrates a perspective view of an exemplary adjustable anatomy table in another vertical configuration, according to one embodiment.

FIG. 5C illustrates an exemplary adjustable anatomy table in another vertical configuration, according to one embodiment. The display 501 is vertically tilted from the horizontal configuration. Unlike the configuration shown in FIGS. 4A and 4B, the display 501 is vertically configured in a landscape mode where the primary axis (longer axis) of the display 501 is positioned in parallel to the ground such that the user can interact with the adjustable anatomy table 500 as if it a white board or a television. The images on the display 501 may be a side view, a top view rotated in 90 degrees, or any other views of a patient's anatomy. Any other views of a patient's specific anatomy (part or full) can be shown on the display 501 without deviating from the scope of the present disclosure.

The landscape mode of the display 501 can be achieved in a variety of ways. In one embodiment, the adjustable anatomy table 500 may have a secondary tilting mechanism (e.g., hinge, a gear mechanism) similar to the tilting mechanism shown in FIGS. 4A and 4B. In another embodiment, the adjustable anatomy table 500 has a single tilting mechanism combined with a rotational mechanism such that the display 501 is vertically tilted as shown in FIG. 5B and further rotated 90 degrees using the rotational mechanism. The order of tilting and rotation can be switched such that the display 501 is first rotated 90 degrees using the rotational mechanism and vertically tilted using the tilting mechanism.

The present adjustable anatomy table is configured to display an anatomy of a human or an animal in a real size. In one embodiment, the present adjustable anatomy table displays an anatomy of a deceased person (e.g., mummy) for a forensic study. Users can interact with the anatomy displayed on the display of the present adjustable anatomy table, For example, A users can dissect, rotate, zoom, and pan the displayed image, select and move a full or partial organ, bone, or any anatomical feature, and apply visual effects (e.g., changing colors, showing annotations). In another embodiment, the present adjustable anatomy table displays a partial human anatomy of an area of specific interest.

The displayed image on the present adjustable anatomy table may be a projected 2D image or 3D rendering of a volumetric image. In one embodiment, the displayed image is radiology reformatted slice images in a gray scale or in a color scale.

In one embodiment, the displayed image is a composite of multiple slice images such as multi-planar reformatting (MPR). MPR reconstructs a volumetric image by stacking the slice images and allows a user to cut slices through the volume in a different plane.

An adjustable anatomy display table has been disclosed. Although various embodiments have been described with respect to specific examples and subsystems, it will be apparent to those of ordinary skill in the art that the concepts disclosed herein are not limited to these specific examples or subsystems but extends to other embodiments as well. Included within the scope of these concepts are all of these other embodiments as specified in the claims that follow.

What is claimed is:

1. An imaging system comprising:
    a display configured to visualize an image of an anatomy in a 1:1 life size of a patient, wherein the display has long sides and short sides;
    a base configured to support the display; and
    an adjustable mechanism that mechanically couples the display to the base,
    wherein the adjustable mechanism is configured to provide a plurality of adjustable positions of the display relative to the base,
    wherein the plurality of adjustable positions include a horizontal position in which the long sides and short sides of the display are in parallel to a ground at a same height, an upright position in which a first short side and a second short side of the short sides of the display are in parallel to the ground at different heights, and a landscape position in which a first long side and a second long side of the long sides of the display are in parallel to the ground at different heights, and
    wherein the adjustable mechanism includes a height adjustable mechanism configured to adjust a height of the display in the upright position.

2. The imaging system of claim 1, wherein the adjustable mechanism further includes a tilting mechanism that is configured to tilt the display from the horizontal position to the upright position.

3. The imaging system of claim 1, wherein the adjustable mechanism further includes a rotational mechanism that is configured to rotate the display about a rotational axis.

4. The imaging system of claim 1, wherein the height adjusting mechanism is configured to adjust the height of the display in the horizontal position.

5. The imaging system of claim 1, wherein the anatomy is a human anatomy, and wherein the display is configured to visualize the human anatomy from a head to a toe.

6. The imaging system of claim 1, wherein the imaging system is configured to receive an input from a user, and wherein the input from the user comprises an input to dissect, rotate, zoom, or pan the image.

7. The imaging system of claim 1, wherein the display is a touch-sensitive display.

8. The imaging system of claim 1, wherein the image is obtained from a medical scanner that is selected from a group comprising a computed tomography (CT) scanner, magnetic resonance (MR) scanner, a positron emission tomography (PET) scanner, a single photon emission computed tomography (SPECT) scanner, an ultrasound scanner.

9. The imaging system of claim 1, wherein the image is obtained from slices of a human body by slicing a cadaver.

10. The imaging system of claim 1, wherein the image is obtained from photographs of cross sections of a human body.

11. The imaging system of claim 1, wherein the image is a radiology reformatted slice image in a gray scale or in a color scale.

12. The imaging system of claim 1, wherein the image is a multi-planar reformatting (MPR) image.

13. The imaging system of claim 1, wherein the image is a three-dimensional (3D) volumetric image.

14. A method comprising:
    providing an imaging system comprising a display, a base, and an adjustable mechanism, wherein the display has long sides and short sides, and the adjustable mechanism mechanically couples the display and the base of the imaging system;
    displaying an image of an anatomy on the display of the imaging system; and
    positioning the display at a plurality of adjustable positions relative to the base using an adjustable mechanism,
    wherein the display is configured to visualize the image of the anatomy in a 1:1 life size of a patient,
    wherein the plurality of adjustable positions include a horizontal position in which the long sides and short sides of the display are in parallel to a ground at a same height, an upright position in which a first short side and a second short side of the short sides of the display are in parallel to the ground at different heights, and a landscape position in which a first long side and a second long side of the long sides of the display are in parallel to the ground at different heights, and wherein the adjustable mechanism includes a height adjustable mechanism configured to adjust a height of the display in the upright position.

15. The method of claim 14, wherein the adjustable mechanism further includes a tilting mechanism that is configured to tilt the display from the horizontal position to the upright position.

16. The method of claim 14, wherein the adjustable mechanism further includes a rotational mechanism that is configured to rotate the display about a rotational axis.

17. The method of claim 14, wherein the anatomy is a human anatomy, and wherein the display is configured to visualize the human anatomy from a head to a toe.

18. The method of claim 14, wherein the image is obtained from one or more of 1) a medical scanner, 2) slices of a human body by slicing a cadaver, 3) photographs of cross sections of a human body, 4) a radiology reformatted slice image, and a multi-planar reformatting (MPR) image.

19. The method of claim 14, wherein the image is a three-dimensional (3D) volumetric image.

\* \* \* \* \*